United States Patent [19]

Mauldin

[11] Patent Number: 4,579,995
[45] Date of Patent: Apr. 1, 1986

[54] PROCESS FOR THE CONVERSION OF METHANOL TO HYDROCARBONS

[75] Inventor: Charles H. Mauldin, Baton Rouge, La.

[73] Assignee: Exxon Research and Engineering Co., Florham Park, N.J.

[21] Appl. No.: 663,680

[22] Filed: Oct. 22, 1984

Related U.S. Application Data

[63] Continuation-in-part of Ser. No. 626,025, Jun. 29, 1984, Pat. No. 4,513,161.

[51] Int. Cl.$^4$ .............................................. C07C 1/00
[52] U.S. Cl. ................... 585/640; 585/469; 585/733; 252/373
[58] Field of Search ............ 585/469, 640, 733; 252/373

[56] References Cited

U.S. PATENT DOCUMENTS

| | | | |
|---|---|---|---|
| 4,049,741 | 9/1977 | Kuo et al. | 585/640 |
| 4,052,477 | 10/1977 | Ireland et al. | 585/640 |
| 4,088,671 | 5/1978 | Kobylinski | 260/449 |
| 4,252,736 | 2/1981 | Haag et al. | 585/733 |
| 4,263,141 | 4/1981 | Möller et al. | 585/733 |
| 4,302,619 | 11/1981 | Gross et al. | 585/733 |
| 4,310,334 | 1/1982 | Waldron | 585/733 |
| 4,338,089 | 7/1982 | Schaper et al. | 518/707 |
| 4,373,109 | 2/1983 | Olah | 585/640 |
| 4,385,193 | 5/1983 | Bijwaard et al. | 585/310 |
| 4,423,274 | 12/1983 | Davidur et al. | 585/640 |
| 4,465,889 | 8/1984 | Anthony et al. | 585/640 |

FOREIGN PATENT DOCUMENTS 2073237  3/1981  United Kingdom ................ 332/385

OTHER PUBLICATIONS

92:129385h; The Synthesis of Solid Hydrocarbons from Methanol; Shima, Kensuke, Morita, Tauyoshi (Miyazaki Univ., Miyazaki, Japan); Nouveau Journal DeChime, vol. 6, No. 10–1982, p. 459.

Fischer–Tropsch Synthesis of Hydrocarbvons over Ruthenium Supported on Transition Metal Oxides; Kikuchi, Nomura, Matsumoto and Morita (Waseda University, Tokyo 160); Pan–Pacific Synfuels Conference, vol. I, Nov. 17–19, 1982 Tokyo, pp. 1–10.

Fischer–Tropsch Synthesis over Titania–Supported Ruthenium Catalysts; Kikuchi Matsumoto, Takahashi, Machino and Morita (Waseda University, 3-4-1 Okubo, Sinjuku, tokyo, Japan); printed in The Netherlands; Applied Catalysis, 10 (1984), pp. 251–260.

IS-T-1006; Hydrogenation of Carbon Monoxide over Ruthenium–Rhenium on Alumina Catalysts; D. E. Whitmoyer (M.S. Thesis submitted to Iowa State University); prepared for the U.S. Department of Energy under Contract No. W-7405-eng-82; Jul. 1982.

Primary Examiner—William R. Dixon, Jr.
Assistant Examiner—Cynthia A. Prezlock
Attorney, Agent, or Firm—Llewellyn A. Proctor

[57] ABSTRACT

A process combination wherein (1) in a first stage wet methanol, or methanol and water, are reacted over a copper-containing methanol synthesis catalyst at conditions sufficient to convert at least a portion of the feed to essentially hydrogen and carbon dioxide and, (2) in a second stage, the product stream from said first stage and methanol are reacted over a cobalt or ruthenium catalyst, or cobalt-containing or ruthenium-containing catalyst, to produce, at reaction conditions, an admixture of $C_{10}^+$ linear paraffin and olefins, which can be further refined and upgraded to high quality middle distillate fuels, and other valuable products such as mogas, diesel fuel, jet fuel, lubes, and specialty solvents, especially premium middle distillate fuels of carbon number ranging from about $C_{10}$ to $C_{20}$.

22 Claims, No Drawings

PROCESS FOR THE CONVERSION OF METHANOL TO HYDROCARBONS

RELATED APPLICATION

This is a continuation-in-part of application Ser. No. 626,025, filed June 29, 1984, now U.S. Pat. No. 4,513,161 titled "Conversion of Methanol to Hydrocarbons."

Reference is also made to application Ser. No. 626,026, filed June 29, 1984, by Mauldin and Payne. This application is titled "Preparation of Liquid Hydrocarbons From Methanol."

BACKGROUND AND PROBLEMS

I. Field of the Invention

This invention relates to a two stage process for the conversion of methanol to hydrocarbons. In particular, it relates to a process wherein, in a first stage, wet methanol, or an admixture of water and methanol, is reacted in the presence of a methanol conversion catalyst to generate hydrogen and carbon dioxide, and, in a second stage, the product of the first stage is contacted in the presence of a methanol-to-hydrocarbon synthesis catalyst with methanol to hydrogenate the methanol and produce $C_{10}^+$ hydrocarbons.

II. Background and Prior Art

In my application Ser. No. 626,025, filed June 29, 1984, there is disclosed a process for the conversion of methanol to $C_{10}^+$ hydrocarbons by reacting methanol with a small amount of hydrogen over a ruthenium catalyst. Specifically, methanol is contacted, in the presence of hydrogen, over a ruthenium-titania catalyst to produce, at reaction conditions, an admixture of $C_{10}^+$ linear paraffins and olefins, which can be further refined and upgraded to high quality middle distillate fuels, and other valuable products such as mogas, diesel fuel, jet fuel, lubes, and specialty solvents, especially premium middle distillate fuels of carbon number ranging from about $C_{10}$ to $C_{20}$. In order to maintain a high rate of selectivity, the mole ratio of methanol:hydrogen is equal to or greater than 2:1, preferably 2:1 to 50:1, and the reaction is conducted at total pressures equal to or greater than about 160 psig, preferably about 160 psig to about 600 psig.

III. Objects

It is the primary objective of this invention to provide further improvements in processes for the production of $C_{10}^+$ hydrocarbons from methanol and hydrogen.

In particular, it is an object to provide a process wherein hydrogen is generated in situ in relatively pure form, or in a form not admixed with any significant amount of a contaminant which would retard or otherwise interfere with the rate of the methanol/hydrogen reaction, and this product is employed to produce $C_{10}^+$ hydrocarbons at high selectivity from methanol and hydrogen.

A specific object is to provide a novel two stage process combination wherein methanol is reacted with water in a first stage to generate a hydrogen-containing product capable of being reacted with methanol to produce $C_{10}^+$ hydrocarbons at high selectivity, and the product then contacted with methanol in a second stage to hydrogenate the methanol and produce $C_{10}^+$ hydrocarbons.

IV. The Invention

These and other objects are achieved in accordance with the present invention, a process combination wherein in a first stage (or, first stage reactor(s)), wet methanol, or methanol and water, are reacted over a methanol conversion catalyst, or methanol synthesis catalyst, preferably a copper-containing catalyst at conditions sufficient to produce, in a methanol hydrolysis reaction, a product consisting essentially of hydrogen and carbon dioxide and, in a second stage (or, second stage reactor(s)), the gaseous mixture of hydrogen and carbon dioxide from said first stage, and methanol, are contacted together in the presence of a methanol-to-hydrocarbon synthesis catalyst, preferably a cobalt or ruthenium catalyst, or cobalt-containing or ruthenium-containing catalyst, and the hydrogen and methanol reacted to produce, at reaction conditions, an admixture of $C_{10}^+$ linear paraffin and olefins. The $C_{10}^+$ hydrocarbons can be further refined and upgraded to high quality middle distillate fuels, and other valuable products such as mogas, diesel fuel, jet fuel, lubes, and specialty solvents; especially premium middle distillate fuels of carbon number ranging from about $C_{10}$ to $C_{20}$.

In reacting wet methanol over a methanol conversion, or methanol synthesis catalyst, hydrogen and carbon dioxide are produced in accordance with the following sequence of known reactions:

$$CH_3OH \rightarrow 2H_2 + CO \quad (1)$$

$$CO + H_2O \rightarrow H_2 + CO_2 \quad (2)$$

$$CH_3OH + H_2O \rightarrow 3H_2 + CO_2 \text{ (overall)} \quad (3)$$

Water, in such reaction sequence (2), converts CO to $CO_2$ via the water gas shift reaction, essentially all of the water being consumed in the reaction The build-up of CO as normally occurs in reaction (1), which has been found to severely inhibit methanol conversion when methanol is reacted over methanol-to-hydrocarbon synthesis catalysts, such as ruthenium catalysts, is thus avoided since essentially all of the CO is converted to $CO_2$ which has not been found to adversely effect the methanol conversion reaction. In accordance with this invention therefore, process conditions are controlled, in a first stage reaction zone, to obtain the optimum conversion of the water and methanol to hydrogen and carbon dioxide to produce an adequate amount of hydrogen for conducting a methanol-to-hydrocarbon synthesis reaction in a subsequent stage. The hydrogen and carbon dioxide product and any unconverted methanol from the first stage reaction zone is passed to the second stage reaction zone wherein the hydrocarbon synthesis reaction is carried out by contacting said product with methanol, in the presence of a methanol-to-hydrocarbon synthesis catalyst, to hydrogenate the methanol and produce $C_{10}^+$ hydrocarbons.

The first stage, or methanol hydrolysis reaction is preferably carried out by reacting methanol and water over a copper-containing methanol conversion, or methanol synthesis catalyst, suitably $Cu-ZnO-Al_2O_3$, $Cu-ZnO-Cr_2O_3$ or the like. The mole ratio of methanol:water is maintained above about 4:1, preferably above about 10:1. Most preferably the mole ratio of methanol:water is maintained within a range of from about 4:1 to about 100:1, and preferably within a range of from about 40:1 to about 80:1. The methanol and water are separately injected, or a mixture of methanol and water is passed over the methanol conversion catalyst at temperatures ranging from about 150° C. to about 300° C., preferably from about 200° C. to about 260° C. and at pressures ranging from about 160 pounds per square inch gauge (psig) to about 800 psig, preferably from about 225 psig to about 500 psig, to convert generally from about 1 to about 15 percent, preferably from about 2 percent to about 10 percent, based on the amount of methanol present in the feed to hydrogen and carbon dioxide. Liquid hourly space velocities range from about 1 $hr^{-1}$ to about 50 $hr^{-1}$, preferably from about 5 $hr^{-1}$ to about 20 $hr^{-1}$.

The product from the first stage reactor, which contains essentially the required amount of hydrogen for hydrogenation of the methanol to be reacted in the second stage reactor, is transferred to the second stage reactor. The product from the first stage reactor plus additional methanol, or unreacted methanol from the first stage, or both, are thus injected or fed into the second stage reactor and catalytically reacted over a cobalt or ruthenium catalyst to produce $C_{10}+$ hydrocarbons. In conducting the second stage reaction, the total pressure must be maintained above about 160 psig, and preferably above about 225 psig, and it is generally desirable to employ methanol, and hydrogen, in molar ratio of $CH_3OH:H_2$ of at least about 2:1 and preferably at least about 4:1 to increase the conversion of methanol to hydrocarbons. Suitably, the $CH_3OH:H_2$ molar ratio ranges from about 2:1 to about 50:1, and preferably the methanol and hydrogen are employed in molar ratio ranging from about 4:1 to about 40:1. In general, the second stage reaction is carried out at liquid hourly space velocities ranging from about 0.1 $hr^{-1}$ to about 10 $hr^{-1}$, preferably from about 0.2 $hr^{-1}$ to about 2 $hr^{-1}$, and at temperatures ranging from about 150° C. to about 350° C., preferably from about 180° C. to about 250° C. Pressures range from about 160 psig to about 800 psig, preferably from about 225 psig to about 500 psig. The product generally and preferably contains 50 percent, or greater, $C_{10}+$ liquid hydrocarbons which boil above about 160° C. (320° F.).

Preferred first stage catalysts, or catalysts suitable for conducting the methanol hydrolysis reaction, are well known. Suitably, such catalysts are constituted of copper, copper and zinc, or copper, zinc, and chromia, optionally supported on a porous refractory inorganic oxide base. Such catalysts may be comprised of a refractory inorganic oxide support, particularly alumina, upon the individual particles of which are impregnated both copper and zinc, the copper in concentration ranging from about 5 to about 25 percent, the zinc in concentration ranging from about 5 to about 25 percent calculated as the respective metal oxides, based upon the total weight of the catalyst composition (dry basis). In its preferred aspects, total metals loadings range to about 50 percent, each metal being calculated as the respective metal oxide, and the ratio of copper:zinc on the catalyst, expressed as the weight percent of the copper oxide relative to the sum total of the copper and zinc oxides, e.g., $CuO/(CuO+ZnO)$, ranges from about 30 percent to about 85 percent. These catalysts possess high selectivity, high activity, and high stability.

The copper, or copper and zinc compounds used to form the catalysts are suitably any inorganic or organometallic material which will decompose, suitably by the application of heat, to provide oxides of the copper, or copper and zinc. Soluble copper and zinc compounds which form solutions from which the compounds can be impregnated onto the solid support, and then subjected to heat decomposition to form the oxide of copper and zinc are preferred. Water soluble copper and zinc salts, are particularly preferred. Exemplary of such materials are organic copper and zinc salts such as the copper or zinc complex salt of acetylacetone, amine salt, and the like. The nitrate salts of copper and zinc are preferred, and provide a readily available, cost-effective means for the impregnation from aqueous solutions of copper and zinc onto a support. For example, an alumina powder can be impregnated with copper and zinc and the impregnated powder formed into different shapes, or the copper and zinc can be impregnated upon a previously prepared support of desired shape, e.g., pills, pellets, tablets, beads, extrudates, sieved particulates, or the like. Pursuant to the impregnation method, the solid porous support in dry state is contacted with a solution of one compound or salt, e.g., a copper salt, and then with a solution of the other compound, or salt, e.g., a zinc salt, or vice versa; or the solid porous support is contacted with a solution containing both the copper and zinc compound, or salts. Preferably the solid porous support is serially contacted with a solution of each of the compounds, or salts, or with a single solution containing both the copper and zinc compounds, or salts, and the solid porous support impregnated via the incipient wetness technique which requires a minimum of solution so that the total solution is absorbed, initially or after some evaporation, or a technique requiring absorption from a dilute or concentrated solution, or solutions, with subsequent filtration or evaporation to effect total uptake of the copper and zinc components. The impregnation can be carried out under a wide range of conditions including ambient or elevated temperatures, and atmospheric or supratmospheric pressures. The copper and zinc impregnated support can thereafter be dried, and calcined.

Alternatively, the catalyst can be prepared in an unsupported form by precipitation methods. For example, the catalyst can be formed by adding together suitable reagents such as the compounds, or salts, of the desirable metal components, e.g., copper, zinc, aluminum, and a base, e.g., sodium hydroxide, sodium carbonate, ammonium hydroxide. The metals form a coprecipitate upon contact with the basic reagent. Catalyst composites containing from about 5 percent to about 70 percent copper oxide, preferably from about 25 percent to about 60 percent copper oxide, and from about 5 percent to about 50 percent zinc oxide, preferably from about 20 percent to about 30 percent zinc oxide, with the balance of the composite comprised of alumina, or chromia, or chromia and alumina, have been found highly effective methanol conversion catalysts.

The copper, or copper/zinc catalyst, after impregnation, or precipitation, can be dried by heating at a temperature above about 25° C., preferably between about 75° C., and about 150° C., in the presence of nitrogen, or oxygen, or both, in an air stream or under vacuum. The catalyst is calcined at a temperature sufficient to decompose the copper and zinc compounds, or salts, and form the oxides of the respective metals. Suitably, the calcination is conducted at temperatures ranging from about 100° C. to about 500° C., preferably from about 200° C. to about 300° C. Excessive temperature, or temperatures above that required to decompose the copper and zinc compounds, or salts, should generally be avoided.

The catalyst is preferably activated by reduction, preferably by contact with hydrogen or a hydrogen-containing gas. Suitably, the reduction is carried out at temperatures ranging from about 200° C. to about 500° C., preferably from about 250° C. to about 350° C.

which fully activates the catalyst while avoiding volatilization and loss of zinc metal from the catalyst.

A preferred cobalt catalyst for use in the second stage reactor is a cobalt-titania catalyst, especially a thoria promoted cobalt-titania catalyst, particularly a cobalt-titania or cobalt-thoria-titania catalyst having a rutile:anatase weight ratio of at least 2:3. The cobalt-titania catalyst, or thoria promoted cobalt-titania catalyst, is one which consists essentially of cobalt, or cobalt and thoria, composited, or dispersed upon titania ($TiO_2$), or a titania-containing carrier, or support. A preferred, and more selective catalyst for use in methanol conversion reactions is one containing titania wherein the rutile: anatase weight ratio ranges from about 2:3 to about 3:2, as determined in accordance with ASTMD 3720-78: Standard Test Method for *Ratio of Anatase to Rutile in Titanium Dioxide Pigments by Use of X-Ray Diffraction*. The cobalt, or cobalt and thoria, is dispersed on the support in catalytically effective amounts. Suitably, in terms of absolute concentration, the cobalt is dispersed on the support in amounts ranging from about 2 percent to about 25 percent, preferably from about 5 percent to about 15 percent, based on the total weight of the catalyst composition (dry basis). The thoria is dispersed on the support in amounts ranging from about 0.1 percent to about 10 percent, preferably from about 0.5 percent to about 5 percent, based on the total weight of the catalyst composition (dry basis). Suitably, the thoria promoted cobalt catalyst contains thoria, $ThO_2$, and cobalt, Co, in ratio of Co:$ThO_2$ ranging from about 1:1 to about 20:1, preferably from about 2:1 to about 15:1, based on the weight of the total amount of $ThO_2$ and Co contained on the catalyst.

The ruthenium-titania catalyst, used in the second stage reactor of the process, is one wherein ruthenium is composited, or dispersed upon titania ($TiO_2$), or a titania-containing carrier, or support in catalytically effective amounts. Suitably, in terms of absolute concentration, the ruthenium is dispersed on the support in amounts ranging from about 0.01 percent to about 8 percent, preferably from about 0.2 percent to about 4 percent, based on the total weight of the catalyst composition (dry basis). These catalyst compositions, it has been found, produce at reaction conditions a product which is predominately $C_{10}^+$ linear paraffins and olefins, with very little oxygenates. These catalysts provide high selectivity, high activity and good activity maintenance in the conversion of methanol to $C_{10}^+$ hydrocarbons.

The cobalt/titania and ruthenium/titania catalysts exhibit high activity and selectivity in the conversion of a feed consisting essentially of methanol, and hydrogen, to $C_{10}^+$ middle distillates. The catalysts employed in the second stage reactor may be prepared by techniques known in the art for the preparation of these and other catalysts. The catalyst can, e.g., be prepared by gellation, or cogellation techniques. Suitably, however, ruthenium can be composited alone, or with another metal, or metals, upon a previously pilled, pelleted, beaded, extruded, or sieved titania or titania-containing support material by the impregnation method. Suitably the cobalt or ruthenium is composited with the support by contacting the support with a solution of a cobalt-containing compound or ruthenium-containing compound, or salt, e.g., a nitrate, chloride or the like. The amount of impregnation solution used should be sufficient to completely immerse the carrier, usually within the range from about 1 to 20 times the carrier by volume, depending on the concentration of the cobalt- or ruthenium-containing compound in the impregnation solution. The impregnation treatment can be carried out under a wide range of conditions including ambient or elevated temperatures. Metal components other than cobalt or ruthenium may also be added as promoters. The introduction of another metal, or metals, into the catalyst can be carried out by any method and at any time of the catalyst preparation, for example, prior to, following or simultaneously with the impregnation of the support with the ruthenium component. In the usual operation, the additional component is introduced simultaneously with the incorporation of the cobalt or ruthenium component.

The cobalt or ruthenium catalyst, after impregnation, is dried by heating at a temperature above about 25° C., preferably between about 65° C., and 150° C., in the presence of nitrogen or oxygen, or both, in an air stream or under vacuum. The metal, or metals, contained on the catalyst can then be reduced. Reduction is performed by contact of the catalyst with hydrogen or a hydrogen-containing gas stream at temperatures ranging from about 180° C. to about 575° C. for periods ranging from about 0.5 to about 24 hours at pressures ranging from ambient to about 40 atmospheres. A gas containing hydrogen and inert components, or a gas containing hydrogen and carbon monoxide in admixture are satisfactory for use in carrying out the reduction.

The invention will be more fully understood by reference to the following examples which present data illustrating its more salient features.

The data which follow were obtained in a small fixed bed reactor unit, conventional material balance workup having been obtained during the runs. All parts are in terms of weight units except as otherwise specified.

The "Schulz-Flory Alpha" is a known method for describing the product distribution in Fischer-Tropsch synthesis reactions, and it is also useful in describing the product distribution from methanol conversion reactions. The Schulz-Flory Alpha is the ratio of the rate of chain propagation to the rate of propagation plus termination, and is described from the plot of ln ($W_n$/n) versus n, where $W_n$ is the weight fraction of product with a carbon number of n. In the examples below, an Alpha value was derived from the $C_{10}/C_{20}$ portion of the product. The Alpha value is indicative of the selectivity of the catalyst for producing heavy hydrocarbons from the methanol, and is indicative of the amount of $C_{10}^+$ hydrocarbons in the product. For example, a Schulz-Flory Alpha of 0.80 corresponds to about 35% by weight of $C_{10}^+$ hydrocarbons in the product, a generally acceptable level of $C_{10}^{30}$ hydrocarbons. A Schulz-Flory Alpha of 0.85, a preferred Alpha value, corresponds to about 54% by weight of $C_{10}^+$ hydrocarbons in the products, and a Schulz-Flory Alpha of 0.90, a more preferred Alpha value, corresponds to about 74% by weight of $C_{10}^+$ hydrocarbons in the product.

The ruthenium-titania catalysts used in the example below were prepared by the following procedure:

Titania (Degussa P-25 $TiO_2$) was used as the support after mixing with sterotex, and after pilling, grinding, and screening to 80-150 mesh (Tyler). The titania was calcined in air and reduced with $H_2$ at 500° C. to provide a support containing a rutile:anatase ratio of 2:1 (ASTM D 3720-78: Standard Test Method for Ratio of Anatase to Rutile in Titanium Dioxide Pigments by Use of X-Ray Diffraction) with a surface area of 23 m²/g and a pore volume of 0.24 ml/gm. Catalysts, of 80-150 mesh size, were prepared by simple impregnation of the support with ruthenium nitrate (Engelhard) from acetone solution using a rotary evaporator, drying in a vacuum oven at 150° C. These catalysts were charged to a reactor, reduced in $H_2$ at 450° C. for one hour, and then reacted with methanol at the conditions described.

In the example which immediately follows methanol and water are reacted over a Cu-ZnO-$Al_2O_3$ catalyst to produce a product constituted essentially of hydrogen and carbon dioxide, and unreacted methanol.

EXAMPLE 1

A run was first conducted using 10:1 methanol/$H_2O$ (by volume) as feed to a methanol hydrolysis reactor. This composition represents a typical raw methanol product as synthesized from methane by existing technology. The raw product is usually distilled by chemical manufacturers to make dry methanol, but this costly distillation is not only unnecessary but is preferably avoided in the fuel-based process of this invention.

The wet methanol was reacted over a Cu-ZnO-$Al_2O_3$ methanol synthesis catalyst manufactured by United Catalysts Inc. (No. L-951). The conditions of the reaction, and the results are shown in Table I.

TABLE I

| Conversion of $CH_3OH/H_2O$ to $H_2/CO_2$ Over Cu—ZnO—$Al_2O_3$ 280 psig, 6 g/hr/g, 10:1 $CH_3OH/H_2O$ (Vol.) | | |
| --- | --- | --- |
| Temperature, °C. | 200 | 250 |
| Conversions | | |
| $CH_3OH$ | 12.5 | 29.9 |
| $H_2O$ | 49.5 | 94.8 |
| Product Composition, Mol. % | | |
| $CH_3OH$ | 58.6 | 34.8 |
| $H_2O$ | 8.5 | 0.7 |
| CO | 0.1 | 5.7 |
| $CO_2$ | 8.3 | 11.8 |
| $H_2$ | 24.5 | 47.0 |

These data show that at 200° C., 3:1 $H_2/CO_2$ is produced as described by reaction (3). Only a trace of CO is present in the product stream. At 250° C., water is consumed to the extent allowed by the thermodynamic equilibrium of reaction (2). Further decomposition of methanol occurs to form $H_2$/CO via reaction (1). It is clear from these data that the copper catalyst is extremely effective in catalyzing the decomposition of methanol to hydrogen and carbon dioxide. Use of sufficient $H_2O$, low temperature, and high space velocity ensures the formation of $CO_2$ instead of CO and produces a product mixture that is suitable as a feed for the hydrocarbon synthesis reactor.

EXAMPLE 2

Carbon monoxide has been found to poison Ru-$TiO_2$ methanol conversion catalysts, and hence suppress the conversion of methanol to hydrocarbons. A run was therefore made to test the effect of $CO_2$ in such reactions. As shown in Table II, the presence of $CO_2$ does not suppress the reaction between methanol and hydrogen in the presence of a Ru-$TiO_2$ catalyst at similar conditions. Essentially the same results, as will be observed, were obtained with $CO_2$ as without $CO_2$.

TABLE II

| Conversion of $CH_3OH/H_2$ to Hydrocarbons Over Ru—$TiO_2$ | | |
| --- | --- | --- |
| | With $CO_2$ | Without $CO_2$ |
| Temperature, °C. | 200 | 250 |
| GHSV, $Hr^{-1}$ | 500 | 500 |
| Inlet Partial Pressure, psia | | |
| $CH_3OH$ | 236 | 236 |
| $H_2$ | 12 | 12 |
| $CO_2$ | 6 | 0 |
| Argon | 41 | 47 |
| $CH_2OH$ Conversion at 35 Hr. | 34 | 31 |
| Carbon Product Distribution, Wt. % | | |
| Co | 8 | 7 |
| $CO_2$ | 11 | 8 |
| Dimethyl ether | 3 | 1 |
| $CH_4$ | 11 | 11 |
| $CH_2^+$ | 67 | 73 |
| % Olefin and Branched in $C_8$ | 37 | 35 |
| Schulz-Flory Alpha | 0.82 | 0.82 |

It is apparent that various modifications and changes can be made without departing the spirit and scope of the invention.

Having described the invention, what is claimed is:

1. A process for the production of hydrocarbon from methanol which comprises contacting methanol and water in molar ratio of methanol:water of from about 4:1 to about 100:1 over a methanol conversion catalyst, in a first reaction zone of a series at temperatures ranging from about 150° C. to about 3 00° C., pressures ranging from about 160 psig to about 800 psig, and space velocities ranging from about 1 $hr^{-1}$ to about 50 $hr^{-1}$ to hydrolyze the methanol and produce a product stream containing hydrogen, carbon dioxide and any unreacted methanol and contacting said product stream in a second reaction zone, in the presence of a methanol-to-hydrocarbon synthesis catalyst, with additional methanol or unreacted methanol from the first stage or both in methanol:hydrogen molar ratio equal to or greater than about 2:1 at total pressure equal to or greater than about 160 psig.

2. The process of claim 1 wherein the methanol conversion catalyst employed in said first reaction zone is one comprised of copper composited with a porous inorganic oxide base.

3. The process of claim 1 wherein the methanol conversion catalyst employed in said first reaction zone is constituted of copper oxide and zinc oxide composited with a refractory inorganic oxide, and has a total copper oxide loading on the catalyst ranging to about 70 percent, and a total zinc oxide loading on the catalyst ranging to about 50 percent.

4. The process of claim 3 wherein the methanol conversion catalyst is supported on a porous refractory inorganic oxide base, and contains from about 5 percent to about 20 percent copper oxide, and from about 5 percent to about 20 percent zinc oxide.

5. The process of claim 4 wherein the methanol conversion catalyst has a total copper oxide and zinc oxide loading on the catalyst ranging from about 10 percent to about 30 percent.

6. The process of claim 3 wherein the methanol conversion catalyst is supported on a porous refractory inorganic oxide base, and has a ratio of CuO/(CuO+ZnO) ranging from about 30 percent to about 85 percent.

7. The process of claim 1 wherein the methanol conversion catalyst contained in the first reaction zone is Cu-ZnO-Al$_2$O$_3$ or Cu-Zno-Cr$_2$O$_3$.

8. The process of claim 1 wherein the temperature of the methanol hydrolysis reaction carried out in said first reaction zone ranges from about 150° C. to about 300° C. the pressure ranges from about 160 psig to about 800 psig, and liquid flow rates ranging from about 1 hr$^{-1}$ to about 50 hr$^{-1}$.

9. The process of claim 1 wherein the methanol to hydrocarbon synthesis catalyst employed in said second reaction zone is constituted of cobalt, or cobalt and thoria in catalytically active amount composited with titania or a titania-containing support.

10. The process of claim 9 wherein the methanol to hydrocarbon synthesis catalyst employed in said second reaction zone is comprised of cobalt dispersed on the support, the catalyst containing from about 2 percent to about 25 percent cobalt, based on the weight of the catalyst composition.

11. The process of claim 10 wherein the catalyst contains from about 5 to about 15 percent cobalt, based on the weight of the catalyst composition.

12. The process of claim 10 wherein the catalyst is comprised of cobalt and thoria dispersed on the support, the catalyst containing from about 2 percent to about 25 percent cobalt, and from about 0.1 percent to about 10 percent thoria, based on the total weight of the catalyst.

13. The process of claim 12 wherein the catalyst is comprised of from about 5 percent to about 15 percent cobalt, and from about 0.5 percent to about 5 percent thoria.

14. The process of claim 1 wherein the methanole-to-hydrocarbon synthesis catalyst employed in said second reaction zone is one which comprises ruthenium or cobalt in catalytically active amount composited with titania or titania-containing support.

15. The process of claim 1 wherein the methanole-to-hydrocarbon synthesis catalyst employed in said second reaction zone contains from about 0.01 percent to about 8 percent ruthenium, based on the weight of the catalyst composition.

16. The process of claim 1 wherein the methanole-to-hydrocarbon synthesis catalyst employed in said second reaction zone contains from about 0.2 to about 4 percent ruthenium, based on the weight of the catalyst composition.

17. The process of claim 1 wherein the molar ratio of methanol:hydrogen fed into the second reaction zone ranges above about 2:1.

18. The process of claim 17 wherein the molar ratio of methanol:hydrogen ranges above about 4:1.

19. The process of claim 1 wherein the total pressure of the reaction in the second reaction zone ranges above about 160 psig.

20. The process of claim 19 wherein the total pressure of the reaction in the second reaction zone ranges from about 160 psig to about 800 psig.

21. The process of claim 1 wherein the conditions of reaction in the second reaction zone are defined within ranges as follows:

| | |
|---|---|
| Methanol:H$_2$ ratio | about 2:1 to 50:1 |
| Liquid Hourly Space Velocities, hr$^{-1}$ | about 0.1 to 10 |
| Temperatures, °C. | about 150 to 350 |
| Total Pressure, psig | about 160 to 800 |

22. The process of claim 21 wherein the reaction conditions are defined within ranges as follows:

| | |
|---|---|
| Methanol:H$_2$ mole ratio | about 4:1 to 40:1 |
| Liquid Hourly Space Velocities, hr$^{-1}$ | about 0.2 to 2 |
| Temperatures, °C. | about 180 to 250 |
| Total Pressure, psig | about 225 to 500 |

* * * * *